United States Patent [19]

Perez-Mendez

[11] Patent Number: 5,596,198
[45] Date of Patent: Jan. 21, 1997

[54] GAMMA RAY CAMERA

[75] Inventor: Victor Perez-Mendez, Berkeley, Calif.

[73] Assignee: The Regents, University of California, Oakland, Calif.

[21] Appl. No.: 231,149

[22] Filed: Apr. 22, 1994

[51] Int. Cl.[6] .......................... G01T 1/164; G01T 1/202
[52] U.S. Cl. ........................ 250/370.11; 250/363.02; 250/366; 250/370.09
[58] Field of Search .................... 250/370.11, 370.09, 250/363.02, 368, 366; 257/428

[56] References Cited

U.S. PATENT DOCUMENTS

| | | | |
|---|---|---|---|
| 4,110,621 | 8/1978 | Horn | 250/370.09 |
| 4,672,207 | 6/1987 | Derenzo | 250/370.11 |
| 4,785,186 | 11/1988 | Street et al. | 250/370.14 |
| 4,879,464 | 11/1989 | Iinuma | 250/361 R |
| 4,906,850 | 3/1990 | Beerlage | 250/370.09 |
| 5,079,426 | 1/1992 | Antonuk et al. | 250/370.14 |
| 5,117,114 | 5/1992 | Street et al. | 250/370.11 |
| 5,138,167 | 8/1992 | Barnes | 250/370.01 |
| 5,144,141 | 9/1992 | Rougeot et al. | 250/370.09 |
| 5,150,394 | 9/1992 | Karellas | 378/62 |
| 5,171,998 | 12/1992 | Engdahl et al. | 250/363.02 |

FOREIGN PATENT DOCUMENTS

WO9301612  1/1993  WIPO .

OTHER PUBLICATIONS

H. Lee et al., "Hydrogenated Amorphous Silicon (a–Si:H) Based Gamma Camera—Monte Carlo Simulations", Jan. 1994, Lawrence Berkley Laboratory, LBL–35050.

*Primary Examiner*—Carolyn E. Fields
*Attorney, Agent, or Firm*—Paul R. Martin; Kathleen Dal Bon; Pepi Ross

[57] ABSTRACT

A gamma ray camera for detecting rays emanating from a radiation source such as an isotope. The gamma ray camera includes a sensor array formed of a visible light crystal for converting incident gamma rays to a plurality of corresponding visible light photons, and a photosensor array responsive to the visible light photons in order to form an electronic image of the radiation therefrom. The photosensor array is adapted to record an integrated amount of charge proportional to the incident gamma rays closest to it, and includes a transparent metallic layer, photodiode consisting of a p-i-n structure formed on one side of the transparent metallic layer, and comprising an upper p-type layer, an intermediate layer and a lower n-type layer. In the preferred mode, the scintillator crystal is composed essentially of a cesium iodide (CsI) crystal preferably doped with a predetermined amount impurity, and the p-type upper intermediate layers and said n-type layer are essentially composed of hydrogenated amorphous silicon (a-Si:H). The gamma ray camera further includes a collimator interposed between the radiation source and the sensor array, and a readout circuit formed on one side of the photosensor array.

23 Claims, 4 Drawing Sheets

GAMMA RAY CAMERA

The subject invention was made with Government support under contract number DE-AC03-76SF00098, between the Department of Energy, and the Regents, University of California. The Government has certain rights in this invention.

BACKGROUND OF THE INVENTION

1. Field of the Invention

The present invention relates in general to gamma ray imaging cameras, and it more particularly relates to such a camera for use in nuclear medicine applications.

2. Background Art

In nuclear medicine, a radioactive isotope is introduced into the area of the body under examination. The radioactive isotope generates gamma rays at certain energies dependent upon the particular isotope used. For example, $^{99m}T_c$ generates gamma rays having an energy of 140 keV which is used in many nuclear medicine applications.

A collimator is then positioned between the patient and the gamma ray imaging camera or detector. The collimator typically comprises a lead plate having a plurality of parallel throughbores so that the gamma rays which pass through the collimator to the imaging detector are essentially parallel to each other.

A single sodium iodide crystal doped with thallium is contained within the housing for the image detector so that gamma rays passing through the collimator pass through an entrance window on the housing and impinge upon the crystal. A thin aluminum sheet across the entrance window hermetically encloses the crystal to protect it from moisture and the elements while a light reflective surface is positioned between the window and the crystal.

The sodium iodide crystal forms the scintillator material and has a typical thickness of between 0.25–0.50 inches. The crystal in turn is glued to a thick glass sheet known as the light pipe. The light pipe not only transmits photons which are generated by the crystal, but also mechanically supports the crystal. In order to detect the emission of photons from the crystal, an array of photomultiplier tubes (PMT) am optically coupled to the light pipe assembly through an optical coupling compound or cement.

In operation, the generated gamma rays pass through the collimator and are absorbed by the sodium iodide crystal. Only very few gamma rays are absorbed by the aluminum sheet across the entrance window due to the low atomic number of the aluminum. Conversely, the relatively high atomic number of the crystal makes it a good absorber of gamma rays. Most of the gamma rays that are of interest to nuclear medicine fall within the energy range of 60–360 keV. These gamma rays interact with the crystal through the photoelectric effect in which a bound electron in the crystal absorbs the gamma ray. Upon doing so, the entire energy of the gamma ray is transferred into kinetic energy of the electron.

The electron which absorbs the energy of the incoming gamma ray transfers this energy to adjacent electrons through coulomb collisions. Many electron-hole pairs are formed in the crystal as a result of the energy deposited by each gamma ray photon. The recombination of the holes in the electrons then creates a large number of low energy scintillation photons. Measurements have shown that for a sodium iodide scintillation crystal, 11.4–13.5% of the total energy from the absorbed energy is emitted as scintillation photons.

The scintillation photons are emitted in random directions by the crystal. Those photons striking the light reflective surface are reflected back towards the photomultiplier tubes so that for each gamma ray absorption, photons are emitted in a conical pattern towards the photomultiplier tubes with a higher concentration of the photons in the center of the cone. These photons are detected by the photomultiplier tubes and, for best possible resolution of the gamma ray absorption, the photons should strike at least seven photomultiplier tubes. Well known electronic circuitry is then employed to determine the position of the gamma ray absorption from the output signals of the photomultiplier tubes.

The scintillation photons travel radially outward from the point of absorption in random directions. The photons travelling towards the photomultiplier tubes are refracted at the crystal/light pipe interface due to a mismatch in the refractive indices for sodium iodide (N=1.85) and glass (N=1.5). Not all of the photons which strike the photomultiplier tubes generate a photoelectron from the photocathode. Instead, the quantum efficiency of the photomultiplier tube is expressed as a percentage, i.e. the percentage of the number of photons striking the photomultiplier tubes which generate a photoelectron from the photocathode.

These previously known gamma ray imaging detectors, however, suffer from a number of disadvantages. One main disadvantage is that the photomultipliers are bulky and heavy, rendering the gamma ray cameras impractical to move around from one location to anther, and to be readily available. Yet a further disadvantage is that the sodium iodide crystal generates only a relatively small number of scintillation photons per absorbed gamma ray. Another disadvantage is that the sodium iodide crystals must be hermetically sealed by the manufacturer in order to protect the crystal from humidity absorption. The sodium crystals are also brittle and can be easily fractured by temperature or thermal shock.

One attempt to resolve some of these problems is described in Engdahl et al., U.S. Pat. No. 5,171,998, which discloses a gamma ray imaging detector having a single scintillation detector crystal which converts absorbed gamma rays into a plurality of scintillation photons. The Engdahl U.S. Pat. No. 5,171,998 patent is incorporated herein by reference. A cesium iodide crystal doped with thallium [CsI(T1)crystal] in place of the sodium iodide crystal as the scintillating detector crystal.

An array of photodiodes is arranged along one side of the crystal to receive the scintillation photons which generate an electrical output signal proportional to the number of scintillation photons received by the photodiode. Diodes with low capacitance and electrical noise, such as silicon drift photodiodes, are employed so that the signal generated by the photodiode as a result of the received scintillation photons is readily detectable above the electrical noise from the photodiodes. An electronic circuitry is then utilized to determine the position of impingement and absorption of the gamma ray.

The PCT patent application. WO93/01612 to Nudelman describes a large area video camera suitable for high energy imaging applications. The sensor-target of the camera tube is composed of T1Br or a two layer structure comprising CsI and a photoconductive layer of materials such as amorphous silicon, amorphous selenium, cadmium sulphide, antimony trisulphide or antimony sulphide oxysulphide. The disclosed tube further deals with problems associated with stray capacitance.

More particularly, this patent describes a low velocity electron beam photoconductive-type video tube which employs novel sensor-target configurations and incorporates a modified electron optical system to acquire large images defined by penetrated ionizing radiation such as X-rays and gamma rays. It is suitable for applications in nuclear medicine, diagnostic radiology and non-destructive testing. In one embodiment, a large area X-ray sensitive video camera tube has a sensor-target including a signal plate for detecting irradiating photons and for providing sufficient storage capacity to hold the electrons on the surface of the signal plate.

The target includes a scintillator which comprises a layer substantially composed of CsI. The CsI layer generates a visible light photon output proportional to the absorbed radiation. A photoconductor which is responsive to the light photon output forms an electronic image of the radiation and comprises a substrate substantially composed of a material selected from the group consisting of amorphous selenium, antimony trisulphide, cadmium sulphide and antimony sulphide oxysulphide. The electron optics of the tube generates a low velocity electron beam which is directed in raster fashion at the photoconductor so that an electronic image from high energy radiation directed at the target is acquired at the signal plate for transmittal to the video readout circuit. This combination comprising a layer of CsI plus an adjacent photoconductive layer is designated as the Cs+ sensor-target.

The CsI layer may be doped with Na or Tl. The CsI layer has a thickness that depends upon the X-ray or gamma ray energy requirement of the application. The large area imaging system may further include an image processor and a film writer to provide a hard copy readout of the electronic image. The tube includes electron optics for generating a low velocity electron beam and directing the beam in raster fashion at the sensor target. The electron beam in tracing out a raster deposits a uniform surface charge of electrons. The sensor-target absorbs the high energy radiation of the imaging beam, causes electrons to be removed and results in a new charge distribution which is an electronic reproduction of the X-ray photon distribution, i.e., the intrinsic X-ray image. The CsI in the scintillator layer may be doped with Na to provide a predominantly blue light emission or alternately Tl which produces a predominantly green light emission.

While the disclosed gamma ray imaging detectors theoretically resolve some of the concerns of conventional devices, such as the elimination of photomultipliers, they do not resolve other significant disadvantages such as the individual recordation of the gamma rays. None of the above patents or other publications disclose a gamma ray camera which is small in size, light in weight, easily transportable, and which integrates the recordation of the gamma rays over the total number of events, rather than individually recording each gamma ray separately.

SUMMARY OF THE INVENTION

It is therefore an object of the present invention to provide a new gamma ray camera which integrates the recordation of gamma rays, over the total number of events.

It is another object of the present invention to provide a new gamma ray camera which is small, light weight, readily transportable and relatively inexpensive to produce.

It is yet another object of the present embodiment to provide a new gamma ray camera which is capable of recording low energy events with high resolution.

The above and further objects of the present invention are achieved by a gamma ray camera for detecting rays emanating from a radiation source such as an isotope. The gamma ray camera includes a sensor array formed of a scintillator crystal for converting incident gamma rays to a plurality of corresponding scintillation photons, and a photosensor array responsive to the scintillation photons in order to form an electronic image of the radiation therefrom.

The photosensor array is adapted to record an integrated amount of charge proportional to the incident gamma rays closest to it, and includes a transparent metallic layer, an amorphous silicon photodiode array with a p-i-n structure, formed on one side of the transparent metallic layer, and comprising an upper p-type layer, an intermediate layer and a lower p-type layer. In the preferred mode, the scintillator crystal is composed essentially of a cesium iodide (CsI) crystal preferably doped with a predetermined amount impurity, and the p-type upper and lower layers and said n-type layer are essentially composed of hydrogenated amorphous silicon (a-Si:H). The gamma ray camera further includes a collimator interposed between the radiation source and the sensor array, and a readout circuit formed on one side of the photosensor array.

In another embodiment, the gamma ray camera further includes a capacitor which is formed of a sandwich-type configuration, and which comprises an upper conductive layer, a lower conductive layer, and an intermediate insulation layer formed therebetween, such that the lower conductive layer overlays the readout circuit. The upper conductive layer and the lower conductive layer of the capacitor are preferably made of Chromium (Cr) or any other metal used in the electronics industry.

The gamma ray camera further includes a preamplifier for amplifying the signals from the sensor array; a processor circuit for processing the signals from the preamplifier in order to generate the desired position coordinates for a gamma ray absorption event; and an image processor for processing signals from the processor circuit, in order to generate corresponding image signals to various peripherals, such as an interactive video display, a film, or a printer.

In another embodiment, the gamma ray camera according to the present invention includes a pixel diode scintillation light detector placed underneath the CsI crystal, and includes an array of pixel diodes. For a high resolution, the CsI crystal is divided into a plurality of generally rectangularly shaped segments, of equal size and dimensions, such that a plurality of gaps are formed therebetween. In the preferred embodiment, these gaps are filled with reflective components such as magnesium oxide, titanium dioxide, or another appropriate metal such as aluminum or silver. This segmentation of the scintillator has the effect of collimating the impinging light photons.

Therefore, the present camera allows the integrated recordation of the events over the entire imaging pattern. As used herein, integration means that the distribution pattern of the gamma rays is recorded on the photodiodes, such that each photodiode will record an integrated amount of charge proportional to the gamma rays closest to it. As a result, the energy resolution is no longer a significant factor, since the imaging pattern is integrated. As a result, a high quality image is obtained without recording each event individually.

In some applications, such as for heart imaging, the gamma rays emanating from the isotope have a relatively low energy, such as 60–70 KeV. Conventional cameras, such as the one disclosed in the Engdhal patent above, do not adequately record the events. However by the using the camera according to the present invention, it is now possible to detect lower energy gamma rays.

In the present camera, it is possible to use a thin CsI crystal-2–5 mm without affecting the sensitivity. In general, the overall thickness of the camera is about 1.5 inches.

BRIEF DESCRIPTION OF THE DRAWINGS

The above and other features of the present invention and the manner of attaining them, will become apparent, and the invention itself will be best understood, by reference to the following description and the accompanying drawings, wherein.

DETAILED DESCRIPTION OF THE PREFERRED EMBODIMENT

Figure 1:
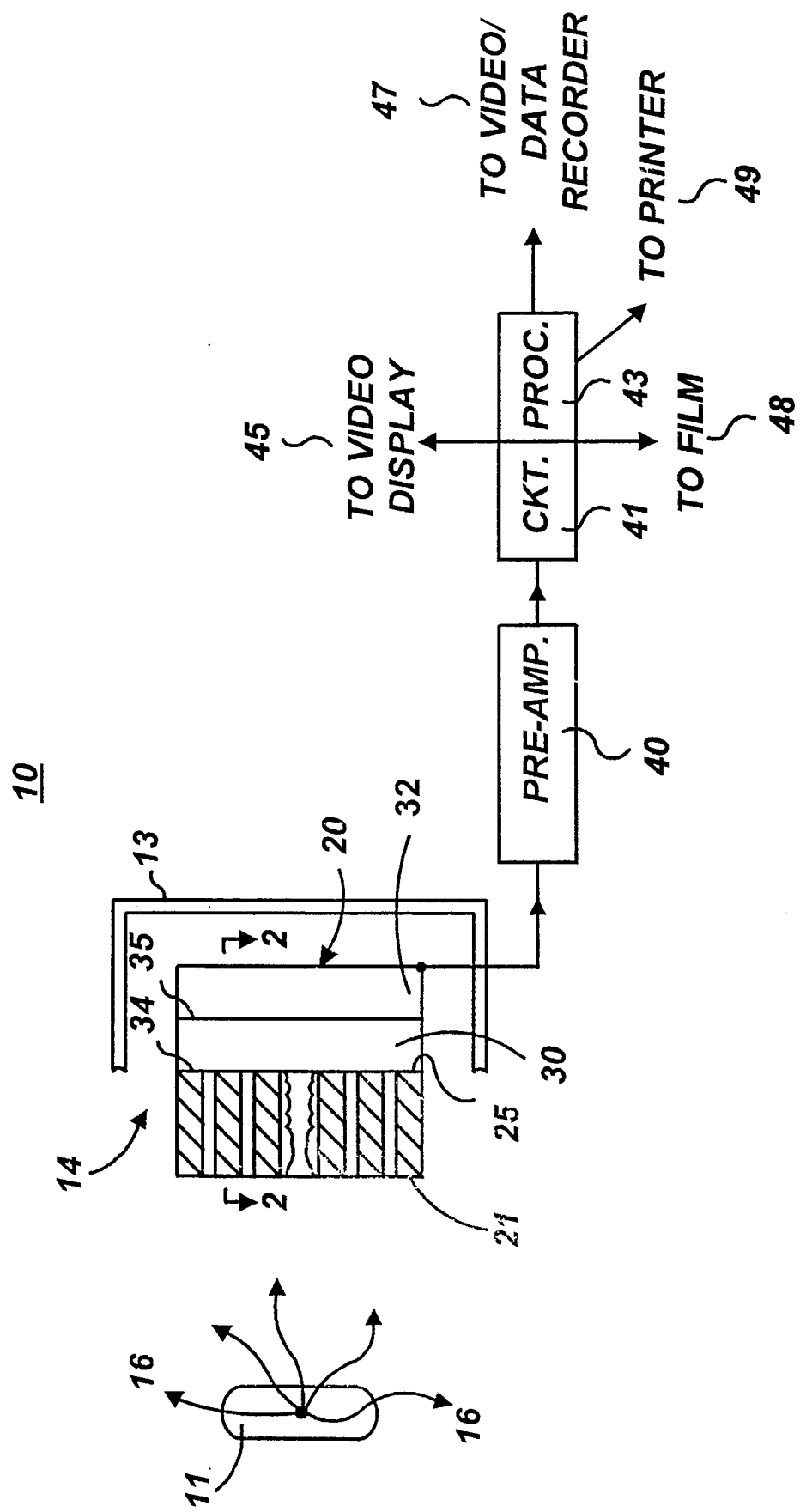
FIG. 1 is a diagrammatic view of a gamma ray camera according to the present invention.

Referring now to the drawings and more particularly to FIG. 1 thereof, there is illustrated a preferred embodiment of a gamma ray camera or detector 10 according to the present invention. The camera 10 is particularly suited, among other applications, for nuclear medicine applications. Typically, a radioactive isotope is introduced into a small body organ 11, such as a heart. During radioactive decay of the isotope, the isotope generates gamma rays 12 in random directions. Some of these gamma rays 12 impinge on and are detected by the camera 10.

The camera 10 generally includes a housing 13 with an entrance window 14 for the gamma rays 12 to pass therethrough and impinge upon a scintillator 30 contained within the housing 13. A collimator 21 is interposed between the body 11 and the window of the gamma my camera 10. For example purposes, and without intending to limit the scope of the present invention, the collimator 21 can be a conventional pinhole collimator, a conventional parallel hole collimator as illustrated in FIG. 1, or can have a new design as will be described hereafter in relation to FIGS. 4 and 4A.

The collimator 21 of FIG. 1 is typically made of lead, and includes a plurality of parallel throughbores 24, which are open on one side 25 to the entrance window 14, and on an opposite side 26 which faces the body 11. The collimator 21 ensures that the gamma rays which pass through it from the body 11 to the window 14 are substantially parallel to each other.

The sensor array 20 is contained within the housing 13 behind the window 14, and includes a scintillator 30 which overlays a photosensor array 32. The scintillator 30 comprises a layer substantially composed of a cesium iodide (CsI) crystal, which may be preferably doped with 1 percent of thallium (Tl), sodium (Na) or similar other impurities. The cesium iodide crystal layer is about 2 to 5 mm thick, although other dimensions are also contemplated.

CsI(Tl) is the preferred scintillation material, since it has a larger light yield than CsI(Na) and is much less hygroscopic. Also, the emission spectrum of CsI(Tl) matches well the quantum efficiency of a-Si:H photosensor array 32, as it will be explained later. Nonetheless, scintillation materials other than CsI can alternatively be used. The scintillator 30 generates a visible light photon output proportional to the absorbed radiation. For this purpose, the scintillator 30 has one of its sides 34 substantially perpendicular to the gamma rays entering the window 14. The other or anterior side 35 of the scintillator 30 overlies the photosensor array 32.

The photosensor array 32 is sensitive to the light photon output from the scintillator 30, and forms an electronic image of the radiation. The composition of the photosensor array 32 is an important part of the present invention, and it will be described later in greater details, with respect to FIGS. 2 and 3.

As further illustrated in FIG. 1, the camera 10 further includes a preamplifier 40 for amplifying the signals from the sensor array 20, and circuitry 41 for processing the signals from the preamplifier 40 in order to generate the desired position coordinates for the gamma ray absorption event. An image processor 43 processes the signals from the circuitry 41 for generating corresponding image signals to various peripherals, such as an interactive video display 45, a video/data recorder 47, a film 48 and/or a printer 49.

Figure 2:
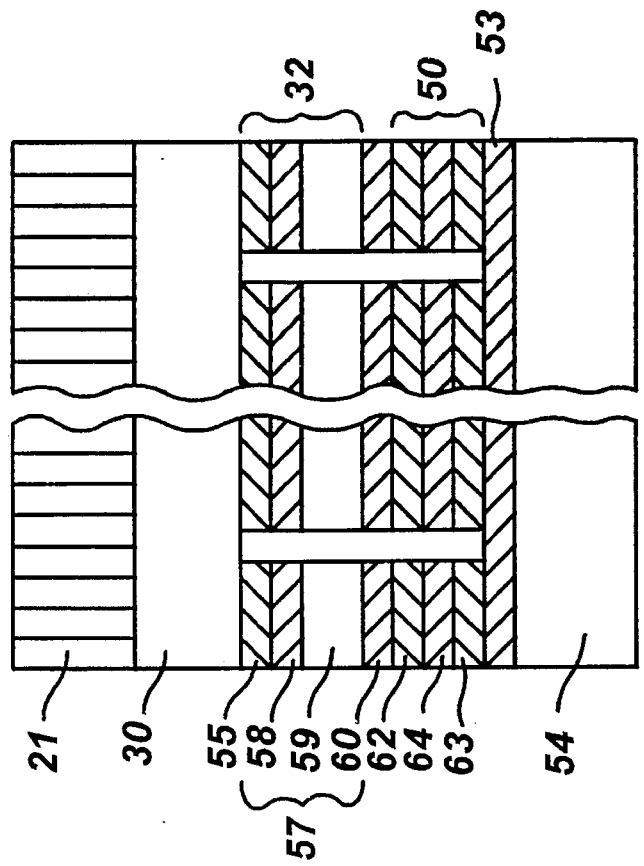
FIG. 2 is an enlarged cross sectional diagrammatic view of the camera of FIG. 1 taken along line 2—2 thereof, according to a preferred embodiment of the present invention.
Figure 3:
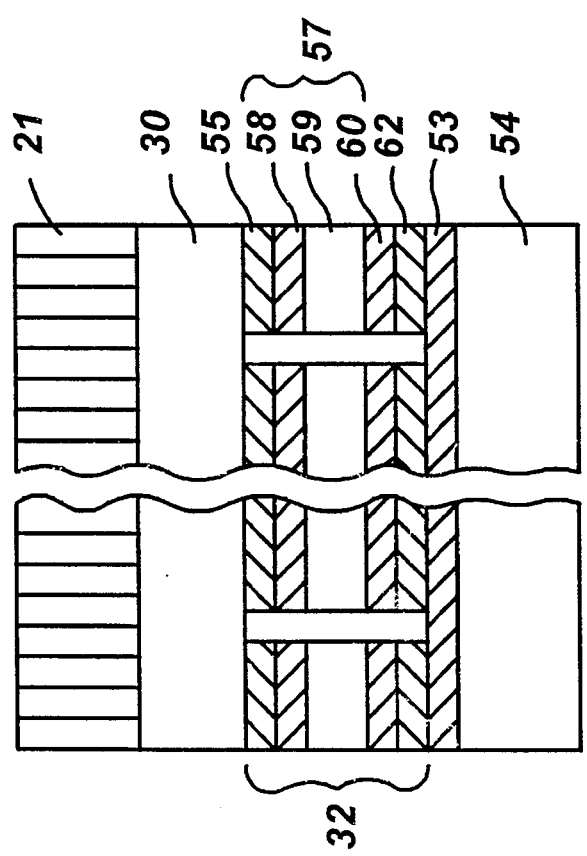
FIG. 3 is an enlarged cross sectional diagrammatic view of the camera of FIG. 1 taken along line 2—2 thereof according to another embodiment of the present invention.

Turning now to FIGS. 2 and 3, they illustrate two diagrammatic cross sectional views of two alternative configurations of the camera 10 according to the present invention. These two configurations are generally similar, and are used for the integration mode operation described herein, with the exception that the configuration of FIG. 2, which is the preferred embodiment, includes an additional storage capacitor 50 for a longer integration time, i.e., 5 minutes.

Starting from top to bottom, FIG. 2 illustrates the collimator 21 overlaid atop the CsI(Tl) scintillator 30, which, in turn, is formed on the photosensor array 32. The latter is formed on a thin transistor film (TFT) readout circuit 53, which is formed on a substrate 54. Therefore, according to the present invention, the photosensor or detector array 32 and the readout circuit 53 are formed on the same substrate and their thickness is in the range of a few micrometers. As a result, the present camera 10, which does not include the conventional bulky photomultipliers is compact, light weight and readily transportable.

Considering now the photosensor array 32 in greater detail, it is comprised of a transparent metallic layer of ITO or tin oxide layer 55 which overlays a p-i-n structure or photodiode 57. The p-i-n structure 57 has a sandwich-type configuration comprising an upper p-type layer 58, an intermediate layer 59 and a lower layer 60 preferably formed of hydrogenated amorphous silicon (a-Si:H), but alternatively selectable from a group of materials of like properties, such as amorphous selenium, antimony trisulphide, cadmium sulphide, antimony sulphide oxysulphide, and crystalline materials such as Si, Ge, gallium arsenide and their alloys.

The lower layer 60 overlays the capacitor 50, which is formed of a sandwich-type configuration, and comprises an upper conductive layer 62 and a lower conductive layer 63 preferably made of Cr, and an intermediate insulation layer 64 formed therebetween. The lower conductive layer 63 overlays the readout circuit 53 which will be described later in more detail, and which is formed on the substrate 54.

As mentioned earlier, the second embodiment of the camera 10, which is diagrammatically illustrated in FIG. 3, is generally similar in design and construction to the preferred embodiment in FIG. 2, with the variation that it does not include the capacitor 50, and thus has a somewhat shorter storage/integration period of the events. The thickness of the p-i-n photodiode 57 for both configurations is about 1 μm, which absorbs about 96% of the light incident on the photodiode 57.

In the integration mode, the signal charge generated in the p-i-n photodiode 57 of the configuration shown in FIG. 3, during the imaging period, is collected by the internal field of the photodiode 57 and stored on the photodiode itself due to its intrinsic capacitance. The integrated signal is readout by the readout circuit 53 from the photodiode 57. In this configuration, the charge decays exponentially with time during the integration period. The charge loss is due to leakage through the photodiode 57 and the readout circuit 53. The charge loss can be reduced by making the readout layer or circuit 53 smaller and by lowering its temperature.

It has been experimentally determined that decay constants of a few tens of seconds with a photodiode capacitance of between 10 and 100 pF were obtained and a gama ray imaging with a 20 second integration time was achieved. In Nuclear medicine, about $10^6$ gamma rays are detected by a gamma camera during approximately 3 minutes of acquisition period. Using this configuration of the camera 10 with pixel size of 1 mm×1 mm×1 μm (105 pF), nine successive readouts with 20 second-integration interval are needed to acquire data for a total acquisition period of 3 minutes.

In the configuration of FIG. 2, the signal charge generated in the p-i-n photodiode 57 is stored in the additional storage capacitor 50. There is substantially no charge leakage, since leakage is blocked by the insulation layer 64, but the thermally generated dark current or noise in the photodiode 57 is also integrated and stored in the capacitor 50. Such thermally generated charge can be measured separately and subtracted from the measured signal. If the thermal generated current is too high, the background charge will saturate the capacitor and the signal charge will not be stored with full efficiency. The thermally generated noise, can be reduced significantly by lowering the ambient temperature of the camera 10, by for instance placing the camera 10 in a refrigerator during operation, in order to maintain the camera 10 at a temperature ranging from −30° C. and 0° C. With this configuration, a 3 minute integration period can be achieved.

Figure 4:
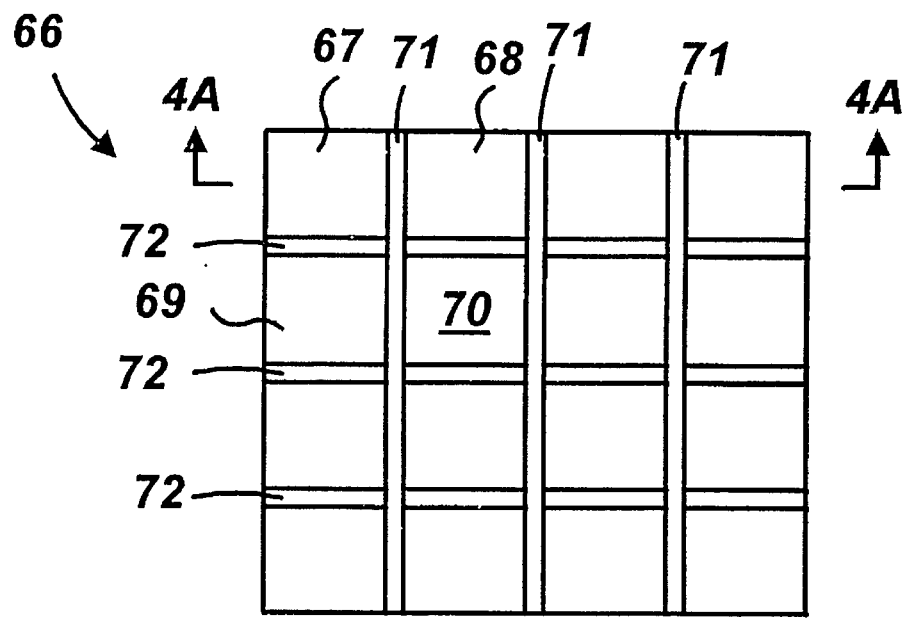
FIG. 4 is an enlarged top plan view of a pixel diode scintillation light detector according to the present invention, for use with an alternative design of the camera of FIG. 1.
Figure 4A:
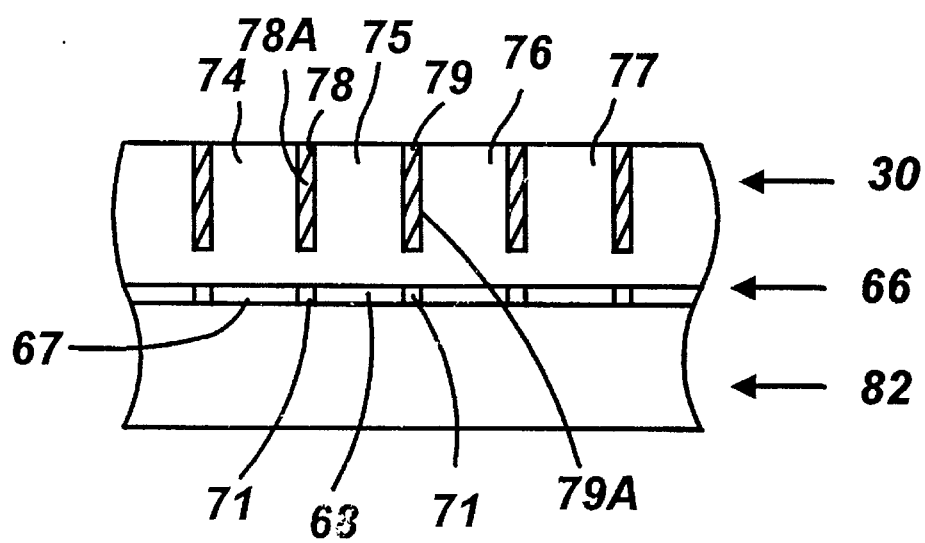
FIG. 4A is a cross-sectional view of the pixel diode scintillation light detector of FIG. 4, shown in position between a crystal layer and a substrate, and taken along line 4A—4A of FIG. 4.

Turning now to FIGS. 4 and 4A, there is illustrated an enlarged top plan view of a pixel diode scintillation light detector 66 according to the present invention. The detector 66 is placed underneath the CsI crystal 30, and includes an array of pixel diodes i.e., 67–70, with separations, i.e. 71, 72 therebetween for circuit interconnection (not shown).

For a high resolution, the CsI crystal 30 is divided into a plurality of segments, i.e. 74, 75, 76, 77, of generally equal size and dimensions, such that a plurality of gaps, i.e., 78, 79 are formed therebetween. In the preferred embodiment, these gaps 78, 79 are filled with reflective components 78A, 79A, such as magnesium oxide, titanium dioxide, or another appropriate metal such as aluminum or silver. This segmentation of the scintillator has the effect of collimating the impinging light photons.

In the preferred embodiment, there is a one-to-one correspondence between the pixel diodes, i.e., 67, 68 and the segments, i.e., 74, 75 of the crystal 30. However, it should be understood that a different relationship is also anticipated by the present invention. In one embodiment, the crystal 30 is about 3 to 5 mm. thick, and the detector 66 is between 1 to 3 microns thick. In order to provide support to the detector 66, a substrate 82 is placed underneath the detector 66.

Figure 5:
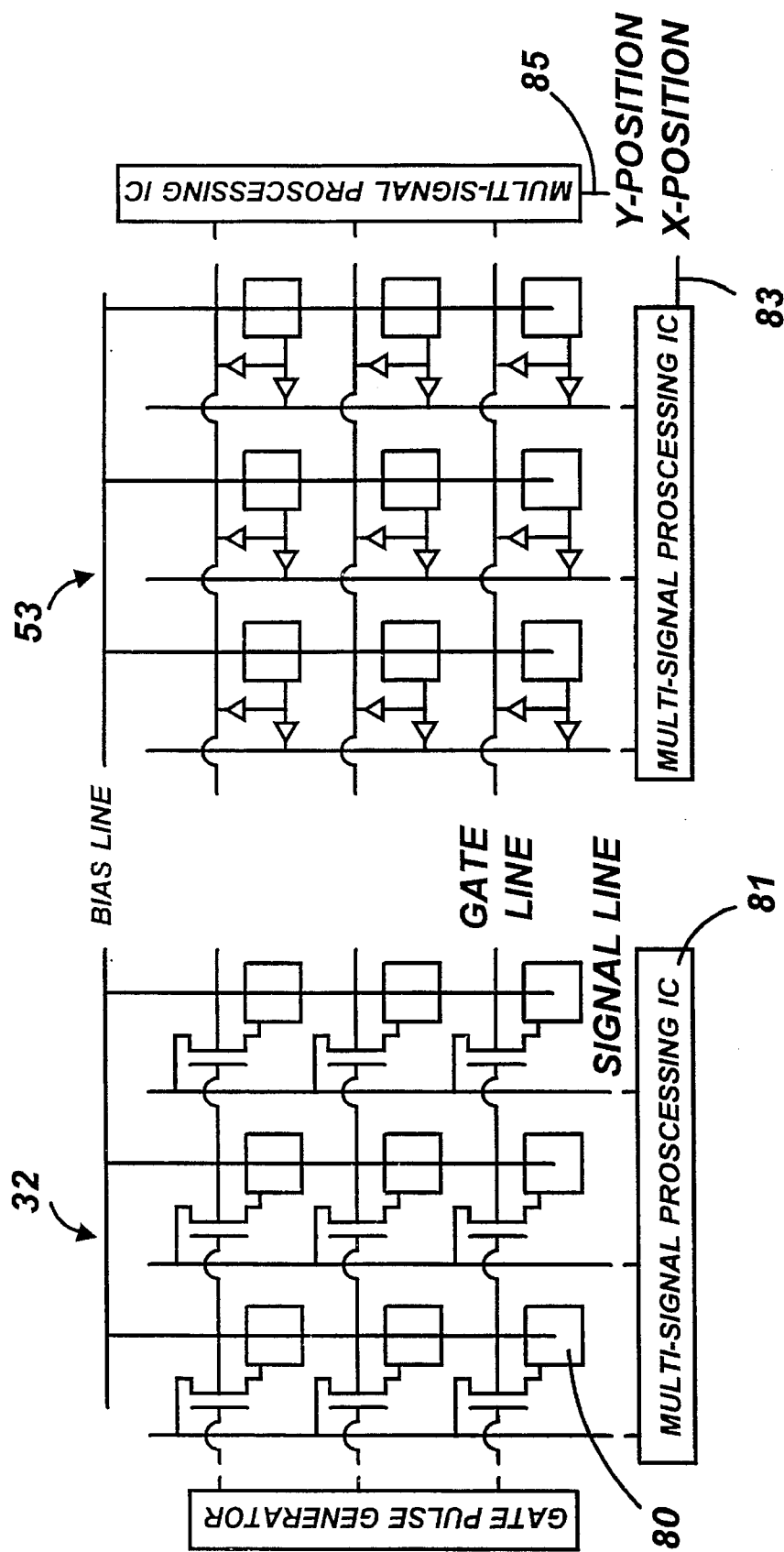
FIG. 5 is schematic circuit diagram of a pixel photosensor array and readout circuit for use in the gamma ray camera of FIG. 1.

Turning now to FIG. 5 there is illustrated a schematic circuit diagram of the pixel photosensor array 32 and the readout circuit 53 for use in the gamma ray camera 10 of FIG. 1. In order to obtain a high fill factor for the photodetector or photosensor array 32, it would be appropriate to form the readout circuit 53 underneath the photosensor array. Depending on the operation scheme there are generally two methods of signal readout: (a) the image scanning readout; and (b) the position detecting readout. In the integration mode the image scanning readout is appropriate, and in the event-by-event collection mode the position detecting readout is suitable.

FIG. 5 shows the schematic diagram of readout circuits for each of these two readout methods. With the image scanning readout scheme, the stored signal on each pixel, i.e., 80, during the integration period, is scanned row-by-row by sequential gate pulses, and sent to an external multisignal processor 81. In the position detecting readout scheme, no switching TFT is required, but each pixel has a charge sensitive amplifier which amplifies the low signal charge generated by an event and sends the output to both X and Y output signal lines 83, 85. This readout scheme can be applied to low event rate such as gamma ray imaging. Whenever a gamma ray is absorbed in the scintillator 32, several a-Si:H pixels, i.e., 80 will be exposed to the light generated in the scintillator 32 and these pixels will produce signal distributions in the X and Y output lines. The pixel position which corresponds to the maximum signal both in the X and Y directions will be the position of the gamma event. By summing all the output signals, the gamma energy can be known and energy selection is possible.

As explained in the report LBL-35050 (UC-414) by the Lawrence Berkeley Laboratory, entitled "Hydrogenated Amorphous Silicon (a-Si:H) Based Gamma Camera—Monte Carlo Simulations", January 1994, which is incorporated herein by reference, Monte Carlo simulation tests were carried out, and the performance of the a-Si:H based gamma camera 10 was investigated. In these simulations, integration mode operation was assumed. As sources $^{99m}$Tc (Eγ=140 keV) and 201Tl (Eγ=70 keV) were used and the phantom was made of water. A Picker LEHR parallel-hole collimator was used. An unsegmented CsI(Tl) single crystal was used as a scintillator. The visible light yield from CsI(Tl) was assumed to be $5.2 \times 10^4$ photons/1 MeV deposited energy and the detector quantum efficiency was set to 70%, which is lower than the reported values of about 80%, hence 70% is a conservative assumption.

The response of the a-Si:H based gamma camera 10 was tested for varying thicknesses of CsI(Tl) and pixel sizes of the photodetectors. A point source of γ in the air was assumed to emit gamma rays which were incident on the scintillator perpendicular to its surface. A 2 mm thick CsI(Tl) is sufficient to absorb the gamma rays from $^{201}$Tl (99% absorbed), while a thicker CsI(Tl) is needed to absorb the gamma rays from $^{99m}$Tc (89% absorbed in 5 mm thick CsI(Tl)).

With $^{99m}$Tc, the resolution is insensitive to CsI(Tl) thickness because of the low cross section of CsI(Tl) at this gamma energy. But with gamma energy of 70 keV from $^{201}$Tl, CsI(Tl) has a high cross section and most of the interactions occur near the top surface, hence the broadening of the visible light is sensitive to the CsI(Tl) thickness. From the above results, a CsI(Tl) crystal of 2 mm and 5 mm thickness is suitable for 70 keV gamma ray imaging and 140 keV gamma ray imaging, respectively.

As the pixel size is reduced the resolution is improved, and with 1 mm×1 mm pixel size, the resolution is 2.2 mm with 70 keV gamma rays and 2 mm thick CsI(Tl), and 1.8 mm with 140 keV gamma rays and 5 mm thick CsI(Tl). Consequently, the intrinsic resolution of the a-Si:H based gamma camera 10 is better than that of the conventional gamma which is 3–4 mm. By reducing the pixel size better resolution can be achieved, but this might not prove to be necessary since the major contributor to the spatial resolution is the collimator.

The water phantom is composed of three regions; hot, warm and cold. Them are no gamma ray sources in the cold region, and the activity of the sources in the warm and hot region is 83.5 kBq/ml and 918.5 kBq/ml, respectively. The distance between the bottom of the warm region and the bottom of the phantom 7 cm, and the hot region is located in the center of the warm region. The bottom of the phantom is in contact with the collimator surface of the gamma camera 10.

In order to investigate the scattering effect in the phantom, the point spread function (PSF) from a point source in the water phantom was simulated. In this simulation the warm and hot regions were removed and a point source with gamma energy of 70 keV or 140 keV was inserted in the phantom. Two different source depths (5 cm and 10 cm) from the collimator surface were used to investigate the effect of source depth in the phantom. For 70 keV gamma rays, gram thick CsI(Tl) was used, and for 140 keV gamma rays, 5 mm thickness was used.

The PSF is composed of two parts. The peak corresponds to the response of the camera and the FWHM is equal to the square root of $R_c^2+R_i^2$, where $R_c$ and $R_i$ are the resolution of the collimator and the scintillator-photodetector, respectively. The exponential tail is used due to the scattering in the phantom. The slope of the tail is dependent on the source depth in the phantom, and as the depth increases the tail broadens.

Due to this scattering, the projection image of distributed sources will be blurred. Even conventional gamma cameras have scattering effects depending on the size of the energy window and there have been many approaches to remove the scattering effects in PET and SPECT images. Most of these methods, however, require information about the energy spectra of the detected gamma rays, which is unavailable in a-Si:H based gamma camera in integration mode. However, using deconvolution methods involving Wiener filters, the blurring effect due to the scattering can be largely reduced.

The source used to obtain the simulated scintigram image with a-Si:H based gamma camera, and the simulated image with a conventional gamma camera, is $^{99m}$Tc and the acquisition time is 3 minutes for both images. For the image with a-Si:H based camera, 128×128 pixels with 1 mm×1 mm pixel size and 5 mm thick CsI(Tl) was used. For the conventional camera the same collimator used for a-Si:H based camera was used and the intrinsic resolution of a ZLC 75 Siemens camera, which is 3.8 mm, was used. The energy window was set to 10% below the source gamma energy, which is a typical value in most cameras. With the same acquisition time the a-Si:H based camera collected more scattered gamma rays than the conventional camera. The number of detected gamma rays in the conventional camera image is $9.6\times10^5$ and in the a-Si:H based camera image is $3.0\times10^6$.

Typical noise sources in a-Si:H based gamma camera are (1) noise due to the random process of radiation emission and absorption; (2) fluctuations in the conversion of gamma ray energy to visible light; and (3) noise by photodiodes and readout electronics. Count-dependent Poisson noise is generally observed in nuclear medicine images and is mainly due to factors (1) and (2) above. The noise generated by factor (3) above is due to 1/f noise, shot noise and thermal noise in the photodiodes and readout electronics, and may be approximated as a Gaussian noise.

Since the current level in the present camera 10 is very low, the 1/f and shot noises are negligible and the thermal noise due to TFT ON-state resistance will be dominant. This thermal noise can be reduced by lowering the temperature of the camera 10. With similar pixel size, the mean value of the noise measured by conventional cameras is about 1.6 fC/pixel. The noise generated by the photosensor array 32 and the readout circuit 53 in the present camera 10 is not important. Moreover this noise can be reduced at lower temperature.

The image obtained with the a-Si:H based gamma camera is degraded by scattering and noise, and this can be mathematically expressed as $$g(x,y)=h(x,y)*f(x,y)+n(x,y) \quad (1)$$

where g(x,y) is the obtained image, f(x,y) is the true object image, h(x,y) is the PSF of the system which contains the blurring effect due to camera resolution and scattering in the phantom, and n(x,y) is the noise in the obtained image. The "*" in Eq. (1) denotes convolution. A simple inverse filtering in the frequency domain is not adequate to restore the image because it will amplify the noise at high frequencies.

A Wiener filter was used to restore the image. The Wiener filter produces the minimum mean-square error between the true object image and the restored image and is often applied to the restoration of nuclear medicine images. The Wiener filter in the frequency domain is expressed by the following equation:

$$WF(u,v)=[1/H(u,v)]\times[|H(u,v)|^2/(|H(u,v)|^2+PN(u,v)/PF(u,v))] \quad (2)$$

where, H(u,v) is the Fourier Transform of the PSF, and PN(u,v) and PF(u,v) represent the power spectrum of the noise and the true object, respectively. The power spectrum of the Poisson noise is a constant equal to the total image count. In the present camera 10, Pn(u,v) was set equal to k*M is the total image count and k is an adjustment factor.

In nuclear medicine the information about the true object power spectrum is generally unknown and several methods have been studied to estimate it. We estimated the true object power spectrum from the obtained image by restoration with a Wiener filter with a constant PN(u,v)/PF(u,v) ratio. The PSF depends on the source depth, and them cannot be only one PSF for 3-dimensionally distributed sources. Usually, the averaged PSF is used in image restoration, hence we used a PSF which is averaged over source depth from 5 cm to 11 cm. The blurring due to scattering is removed and the overall image quality is improved compared to the image obtained with a conventional gamma camera. A better image quality is obtained with the a-Si:H based camera 10 compared to the image obtained with the conventional gamma cameras.

The foregoing description of the preferred embodiments has been presented for purposes of illustration and description. It is not intended to be exhaustive or to limit the invention to the precise forms described, and obviously many other modifications are possible in light of the above teaching. The embodiments were chosen in order to explain most clearly the principles of the invention and its practical applications, thereby to enable others in the art to utilize most effectively the invention in various other embodiments and with various other modifications as may be suited to the particular use contemplated.

What is claimed:

1. A gamma ray camera for detecting rays emanating from a radiation source, the gamma ray camera comprising in combination:
   (a) a scintillator crystal for converting incident gamma rays to a plurality of corresponding scintillation photons, and including a scintillation layer; and
   (b) a photosensor array disposed in direct contact with one side of said scintillator crystal, and responsive to the scintillation photons in order to form an electronic pattern of the incident gamma rays by recording an integrated amount of charge proportional to the incident gamma rays, without counting individual gamma rays, said photosensor array including:
       (i) a transparent metallic layer; and
       (ii) a p-i-n structure formed on one side of said transparent metallic layer, having a sandwich-type configuration, and comprising an upper p-type layer, an intermediate intrinsic layer and a lower n-type layer;
   (c) a collimator interposed between the radiation source and said scintillation crystal; and
   (d) a readout circuit formed on one side of said lower n-type layer.

2. The gamma ray camera according to claim 1, wherein said scintillation layer is composed essentially of a cesium iodide (CsI) crystal doped with a predetermined amount of impurity; and
   wherein said upper p-type layer, intermediate intrinsic layer, and lower n-type layer are essentially composed of hydrogenated amorphous silicon (a-Si:H).

3. The gamma ray camera according to claim 2, wherein said cesium iodide crystal layer of said scintillator crystal is doped with 0.1–5 percent of thallium (Tl).

4. The gamma ray camera according to claim 2, wherein said cesium iodide crystal layer of said scintillator crystal is doped with 0.1–5 percent of sodium (Na).

5. The gamma ray camera according to claim 2, wherein said cesium iodide crystal layer is about 2 to 5 mm thick.

6. The gamma ray camera according to claim 2, further including a capacitor which is formed of a sandwich-type configuration, and which comprises an upper conductive layer, a lower conductive layer, and an intermediate insulation layer formed therebetween; and
   wherein said lower conductive layer overlays said readout circuit.

7. The gamma ray camera according to claim 6, wherein said upper conductive layer and said lower conductive layer of said capacitor are made of chromium (Cr).

8. The gamma ray camera according to claim 6, wherein said readout circuit includes a thin transistor film (TFT) readout circuit formed on a substrate.

9. The gamma ray camera according to claim 8, wherein said transparent metallic layer is made of ITO (indium tin oxide).

10. The gamma ray camera according to claim 8, wherein said transparent metallic layer is made of tin oxide.

11. The gamma ray camera according to claim 8, wherein said collimator includes a plurality of parallel throughbores for ensuring that the gamma rays passing therethrough from the radiation source to said photosensor array are substantially parallel to each other.

12. The gamma ray camera according to claim 11, wherein the collimator is a pinhole collimator.

13. The gamma ray camera according to claim 11, wherein the collimator is a parallel hole collimator.

14. The gamma ray camera according to claim 1, wherein said scintillation layer is composed essentially of a cesium iodide (CsI) crystal doped with a predetermined amount impurity; and
   wherein said upper p-type layer, intermediate intrinsic layer, and lower n-type layer are selected from a group consisting of amorphous selenium, amorphous Ge and a p-i-n doped crystal semiconductor.

15. The gamma ray camera according to claim 1, wherein said readout circuit is maintained at a low temperature in order to reduce charge decay during integration.

16. The gamma ray camera according to claim 8, further including a preamplifier for amplifying the signals from said photosensor array; and
   a processor circuit for processing the signals from said preamplifier in order to generate the desired position coordinates for a gamma ray absorption event.

17. The gamma ray camera according to claim 16 further including an image processor for processing signals from said processor circuit, for generating corresponding image signals to various peripherals.

18. The gamma ray camera according to claim 17, wherein said peripherals include an interactive video display.

19. The gamma ray camera according to claim 1 wherein said scintillator crystal includes a cesium iodide (CsI) crystal doped with a predetermined amount of impurity;
   wherein said photosensor array includes a pixel diode scintillation light detector formed underneath said CsI crystal; and
   wherein said CsI crystal is segmented into a plurality of individual segments, said segments being separated by a plurality of corresponding gaps filled with a reflective material for collimating the rays emanating from the radiation source.

20. The gamma ray camera according to claim 19, wherein each segment is generally rectangularly shaped.

21. The gamma ray camera according to claim 20, wherein each segment has a side dimension of about two millimeters.

22. The gamma ray camera according to claim 21, wherein said reflective material includes a metallic material.

23. The gamma ray camera according to claim 22, wherein said reflective material is selected from a group consisting of magnesium oxide, titanium dioxide, aluminum, silver, chromium, gold, platinum, or nickel.

* * * * *